United States Patent
Oosawa (10) Patent No.: US 10,295,619 B2
(45) Date of Patent: May 21, 2019

(54) BED APPARATUS FOR MAGNETIC RESONANCE IMAGING APPARATUS AND MAGNETIC RESONANCE IMAGING APPARATUS

(71) Applicant: Takuhiro Oosawa, Yaita (JP)

(72) Inventor: Takuhiro Oosawa, Yaita (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1351 days.

(21) Appl. No.: 13/737,176

(22) Filed: Jan. 9, 2013

(65) Prior Publication Data

US 2013/0176029 A1    Jul. 11, 2013

(30) Foreign Application Priority Data

Jan. 10, 2012   (JP) ................................ 2012-001738
Nov. 6, 2012    (JP) ................................ 2012-244243

(51) Int. Cl.
  *G01R 33/30*   (2006.01)
  *A61B 5/055*   (2006.01)
  *G01R 33/36*   (2006.01)

(52) U.S. Cl.
  CPC ............ *G01R 33/30* (2013.01); *A61B 5/0555* (2013.01); *G01R 33/36* (2013.01)

(58) Field of Classification Search
  CPC .... G01R 33/30; G01R 33/36; G01R 33/3621; G01R 33/34007; G01R 33/56375; G01R 33/56383; A61B 5/0555
  USPC ................................................. 324/318–322
  See application file for complete search history.

(56) References Cited

U.S. PATENT DOCUMENTS

| | | | |
|---|---|---|---|
| 5,065,760 A | 11/1991 | Krause et al. | |
| 5,210,893 A | 5/1993 | Uosaki et al. | |
| 5,474,068 A * | 12/1995 | Takamori ................. | A61B 6/56 242/378.2 |
| 7,719,271 B2 | 5/2010 | Ohsawa | |

(Continued)

FOREIGN PATENT DOCUMENTS

| JP | 62(1987)-172227 U | 10/1987 |
|---|---|---|
| JP | 4040939 | 2/1992 |

(Continued)

OTHER PUBLICATIONS

Takuhiro, Oosawa; English translation of JP H04-40939; translation provided by Espacenet on Aug. 11, 2016.*

(Continued)

*Primary Examiner* — Rishi R Patel
(74) *Attorney, Agent, or Firm* — Nixon & Vanderhye P.C.

(57) ABSTRACT

According to one embodiment, a bed apparatus for a magnetic resonance imaging apparatus includes a table, a table driving mechanism, a bed supporting part, and a cable guide. The table provides a connection port for a reception coil of magnetic resonance signals. The table driving mechanism is configured to shift the table. The bed supporting part is configured to support the table. The cable guide is configured to protect a signal cable between the table and the bed supporting part and to bend a portion of the signal cable along with a move of the table. The signal cable is connected to the connection port. The portion of the signal cable corresponds to a position of the table.

9 Claims, 5 Drawing Sheets

(56) References Cited

U.S. PATENT DOCUMENTS

| | | | |
|---|---|---|---|
| 8,467,847 B2* | 6/2013 | Caruba | A61B 5/0035 600/411 |
| 2007/0035301 A1* | 2/2007 | Nakabayashi | G01R 33/28 324/318 |
| 2007/0143921 A1* | 6/2007 | Hiyama | A61B 5/0555 5/601 |
| 2008/0030195 A1* | 2/2008 | Hagen | G01R 33/36 324/322 |
| 2008/0106262 A1* | 5/2008 | Ohsawa | G01R 33/34007 324/318 |

FOREIGN PATENT DOCUMENTS

| | | |
|---|---|---|
| JP | 9-047443 | 2/1997 |
| JP | 2008-012290 | 1/2008 |

OTHER PUBLICATIONS

Office Action dated Jul. 5, 2016 in JP Patent Application No. 2012-244243.

Office Action dated Jul. 17, 2014 in CN Patent Application No. 201310002446.3; and *partial English translation, which describes JPS62(1987)-172227U.

* cited by examiner

BED APPARATUS FOR MAGNETIC RESONANCE IMAGING APPARATUS AND MAGNETIC RESONANCE IMAGING APPARATUS

CROSS REFERENCES TO RELATED APPLICATION

This application is based upon and claims the benefit of priorities from Japanese Patent Application No. 2012-001738 filed on Jan. 10, 2012 and Japanese Patent Application No. 2012-244243 filed on Nov. 6, 2012; the entire contents of Japanese Patent Application No. 2012-001738 and Japanese Patent Application No. 2012-244243 are incorporated herein by reference.

FIELD

Embodiments described herein relate generally to a bed apparatus for an MRI (magnetic resonance imaging) apparatus and a magnetic resonance imaging apparatus.

BACKGROUND

The MRI apparatus is an image diagnostic apparatus which excites nuclear spins in an object set in a static magnetic field magnetically with RF (radio frequency) signals having the Larmor frequency and reconstructs an MR image based on MR (magnetic resonance) signals generated due to the excitation. In regard to a bed used for the MRI apparatus, a type having a connection port for a reception coil of MR signals on the table for setting an object is mainly used from the perspective of operability and safety.

However, when a connection port of reception coil is provided on the table of the bed, it becomes required to connect the table, which is a moving part, with the table driving mechanism by a signal cable. Consequently, there is a problem that the structure of the bed becomes complicated since a guard and a guide of the signal cable are required.

Accordingly, it is an object of the present invention to provide a bed apparatus for a magnetic resonance imaging apparatus and a magnetic resonance imaging apparatus which can provide a connection port for a reception coil of MR signals on the table with a simpler structure.

DETAILED DESCRIPTION

In general, according to one embodiment, a bed apparatus for a magnetic resonance imaging apparatus includes a table, a table driving mechanism, a bed supporting part, and a cable guide. The table provides a connection port for a reception coil of magnetic resonance signals. The table driving mechanism is configured to shift the table. The bed supporting part is configured to support the table. The cable guide is configured to protect a signal cable between the table and the bed supporting part and to bend a portion of the signal cable along with a move of the table. The signal cable is connected to the connection port. The portion of the signal cable corresponds to a position of the table.

Further, according to one embodiment, a magnetic resonance imaging apparatus includes the bed apparatus and an imaging part. The imaging part is configured to image an object set on the bed apparatus.

A bed apparatus for a magnetic resonance imaging apparatus and a magnetic resonance imaging apparatus according to embodiments of the present invention will be described with reference to the accompanying drawings.

Figure 1:
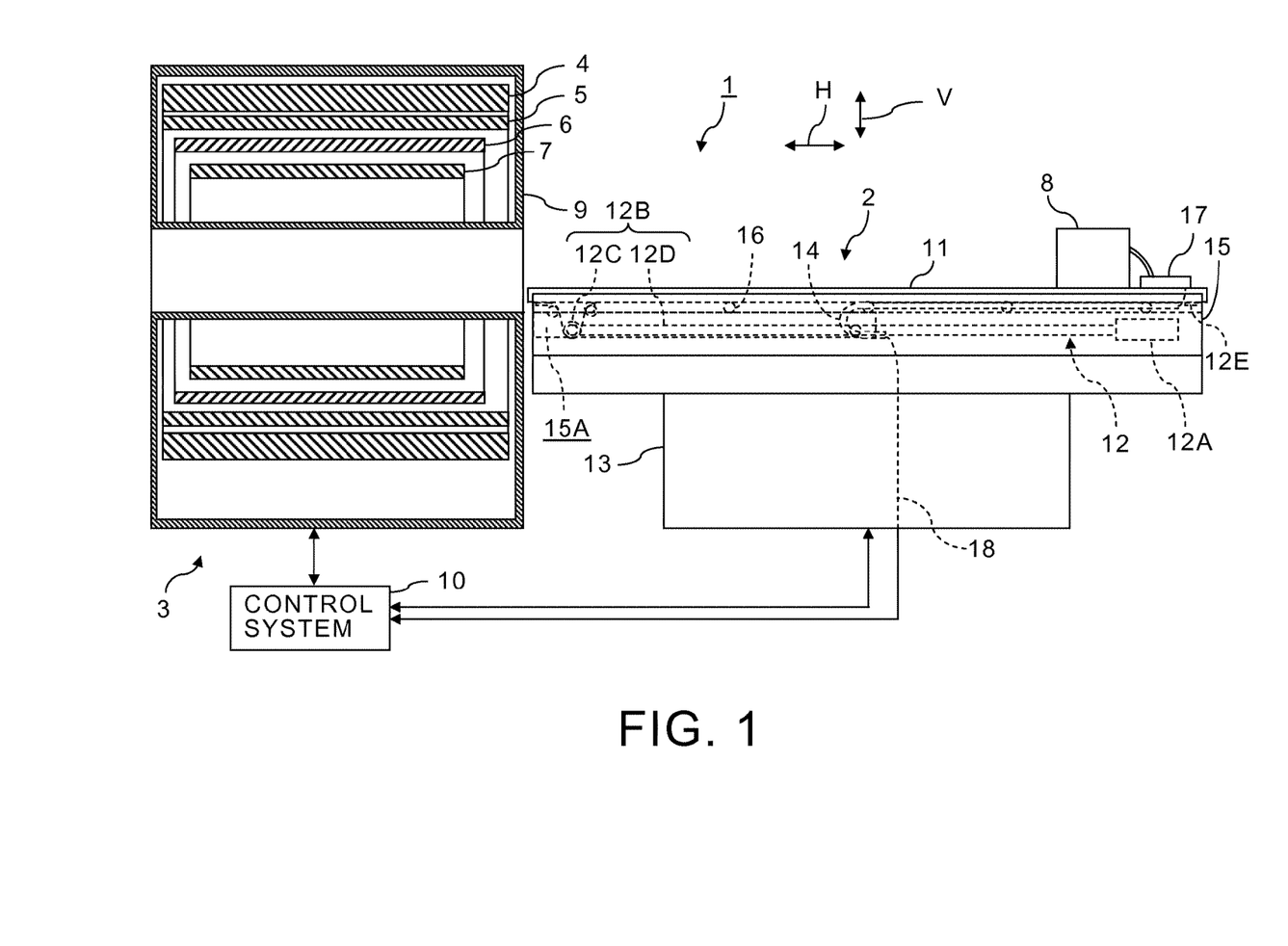
FIG. 1 is a configuration diagram of a bed apparatus and a magnetic resonance imaging apparatus according to an embodiment of the present invention.

FIG. 1 is a configuration diagram of a bed apparatus and a magnetic resonance imaging apparatus according to an embodiment of the present invention.

The magnetic resonance imaging apparatus 1 includes a bed apparatus 2 and an imaging part 3. The imaging part 3 is a system to perform imaging of an object set on the bed apparatus 2. Specifically, the imaging part 3 has a static magnetic field magnet 4, a shim coil 5, a gradient coil 6, a whole body coil (WBC) 7, a coil 8 for receiving MR signals, a gantry 9 and a control system 10. The static magnetic field magnet 4, the shim coil 5, the gradient coil 6 and the WBC 7 are built in the gantry 9.

The control system 10 controls the bed apparatus 2, the static magnetic field magnet 4, the shim coil 5, the gradient coil 6 and the WBC 7 according to imaging conditions and generates MR image data based on MR signals received by the RF coil 8 for receiving MR signals. For that purpose, the control system 10 includes: a static magnetic field power supply, a shim coil power supply and a gradient magnetic field power supply which supply electrical power to the static magnetic field magnet 4, the shim coil 5 and the gradient coil 6 respectively; a transmitter which outputs RF signals to the WBC 7; a receiver which receives MR signals from the RF coil 8 for receiving MR signals; a sequence controller; and a computer.

The sequence controller is a control unit to control the gradient magnetic field power supply, the transmitter and the receiver according to a pulse sequence. Furthermore, the computer controls the sequence controller and generates MR image data based on MR signals.

On the other hand, the bed apparatus 2 includes a table 11, a table driving mechanism 12, a bed supporting part 13 and a cable guide 14. The bed supporting part 13 is the main body of bed apparatus 2 for moving table 11 in the vertical direction while supporting table 11. The bed supporting part 13 has a bed exterior 15 for supporting table 11. Furthermore, the table driving mechanism 12 has a function to move table 11 in the horizontal direction H toward an imaging region formed in gantry 9.

Wheels 16 are mounted on the undersurface side of the table 11. Furthermore, a connection port 17 for a reception coil is provided on the upper surface side of the table 11. The connection port 17 is connected to the receiver in the control system 10 via signal cables 18. Then, an object can be set on the table 11 and the table 11 can be moved in the imaging region in the gantry 9 in the state that the reception RF coil 8 has been connected to the connection port 17. That is, the bed apparatus 2 is a device of the type in which the connection port 17 of the RF coil 8 has been provided on the table 11.

Furthermore, the cable guide 14 is a cylindrical member, which has flexibility, for protecting the signal cables 18, connected to the connection port 17, between the table 11 and the bed supporting part 13.

For example, the cable guide 14 can be configured by mutually connecting tubal members, of which both ends are open, with connection members. More specifically, adjacent tubal members out of the tubal members are connected mutually by the connection member while leaving a gap between the adjacent tubal members. Consequently, one of the adjacent tubal members can be inclined to the other. That is, the whole cable guide 14 can become flexible.

Figure 2:
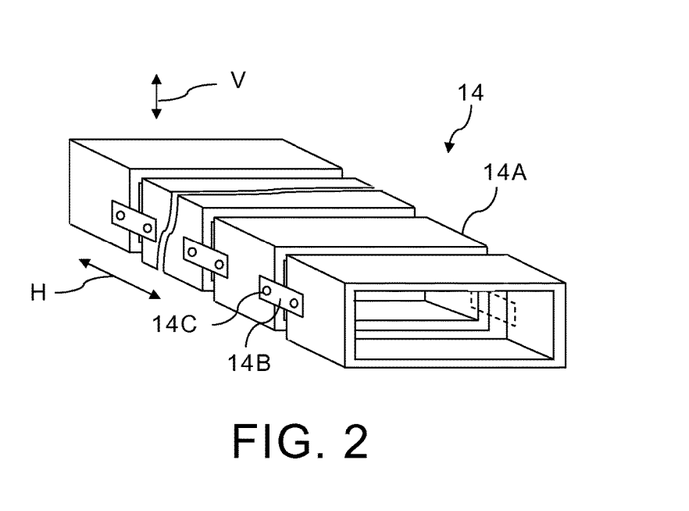
FIG. 2 is a perspective view to show a structural example of the cable guide shown in FIG. 1.

FIG. 2 is a perspective view to show a structural example of the cable guide 14 shown in FIG. 1.

As shown in FIG. 2, the cable guide 14 can be configured by connecting plural rectangular tubes 14A, whose both ends are open, with plate connection members 14B. The rectangular tubes 14A are connected rotatably with the connection members 14B by shafts 14C. Furthermore, a gap is set aside between adjacent rectangular tubes 14A. Accordingly, the cable guide 14 has flexibility in the vertical direction V. That is, the cable guide 14 can be bent.

Figure 3:
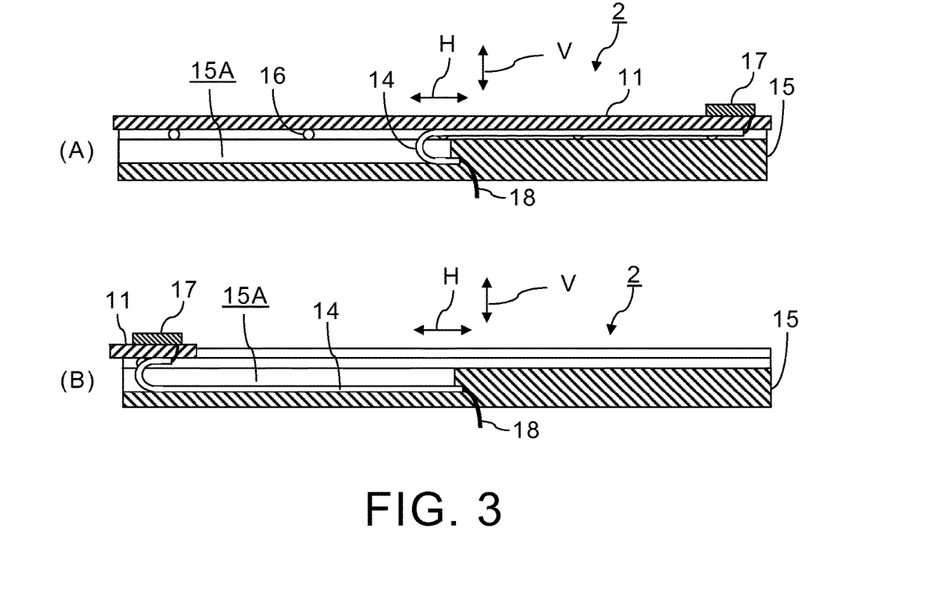
FIG. 3 shows the operation of the cable guide in the case of moving the table of the bed apparatus shown in FIG. 1.

FIG. 3 shows the operation of the cable guide 14 in the case of moving the table 11 of the bed apparatus 2 shown in FIG. 1.

FIG. 3 (A) shows the state of the cable guide 14 when the table 11 is at the out limit position farthest from the gantry 9. Meanwhile, FIG. 3 (B) shows the state of the cable guide 14 in the state that the table 11 has been sent into the gantry 9.

As shown in (A) and (B) of FIG. 3, the cable guide 14 is arranged so that a portion corresponding to the position of table 11 is bent in the vertical direction V along with movement of table 11. Specifically, one end of cable guide 14 is connected to the undersurface of the end part of table 11 in the opposite side to gantry 9. Then, the cable guide 14 is bent in the downward direction. Further, the other end of cable guide 14 is connected to the bed supporting part 13 side.

Consequently, a changing portion of the cable guide 14 becomes constantly bending in the vertical direction V. Then, the bending portion of cable guide 14 changes according to the position of table 11.

Furthermore, the cable guide 14 bends portions of the signal cables 18 according to the position of the table 11. Especially, the cable guide 14 bends the portions of the signal cables 18 in the same direction regardless of the position of the table 11 in the longitudinal direction. In the example shown by figures, the portions of the signal cables 18 are bent in the vertical direction by the cable guide 14.

The length of the cable guide 14 can be determined based on the stroke of the table 11 and the length of the table 11 in the longitudinal direction. The stroke of the table 11 is determined so that a part of the table 11, with which the cable guide 14 is connected, becomes above the bed supporting part 13 when the table 11 has been moved to the limit position of the gantry 9 side. Accordingly, the connection port 17, for a reception coil, connected to the end part of the cable guide 14 across the table 11 is also arranged on the upper surface of the end part of the table 11 in the opposite side to the gantry 9.

Therefore, the length of the cable guide 14 can be determined so that the cable guide 14 becomes constantly doubled back on itself wherever the table 11 is moved within the stroke range. Furthermore, when the end part of the cable guide 14 in the bed supporting part 13 side is fixed to the center of the bed supporting part 13, the movable range of the table 11 can be secured while shortening the length of the cable guide 14.

Note that, the respective figures including FIG. 3 show the example in which the end part of the cable guide 14 in the bed supporting part 13 side is fixed to the bed exterior 15. However, the end part of the cable guide 14 in the bed supporting part 13 side may be fixed to an arbitrary element of the bed supporting part 13 via arbitrary connection members.

On the other hand, a concave portion 15A for guiding the cable guide 14 can be made in the bed exterior 15 of the bed supporting part 13.

Figure 4:
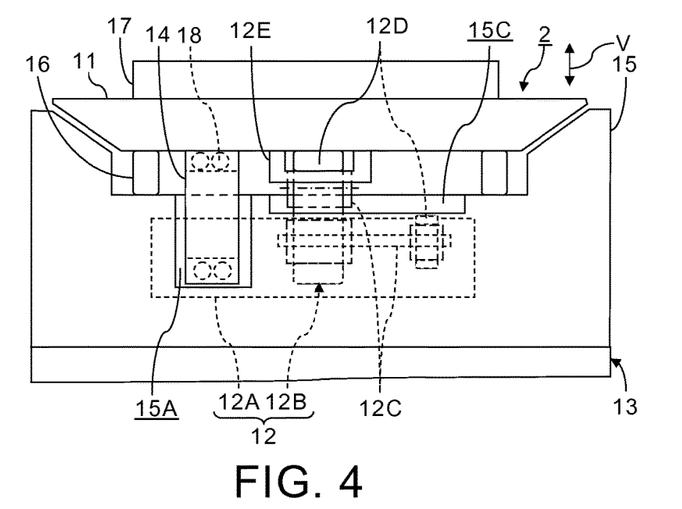
FIG. 4 is a left side view to show a detailed configuration example of the bed apparatus shown in FIG. 1.
Figure 5:
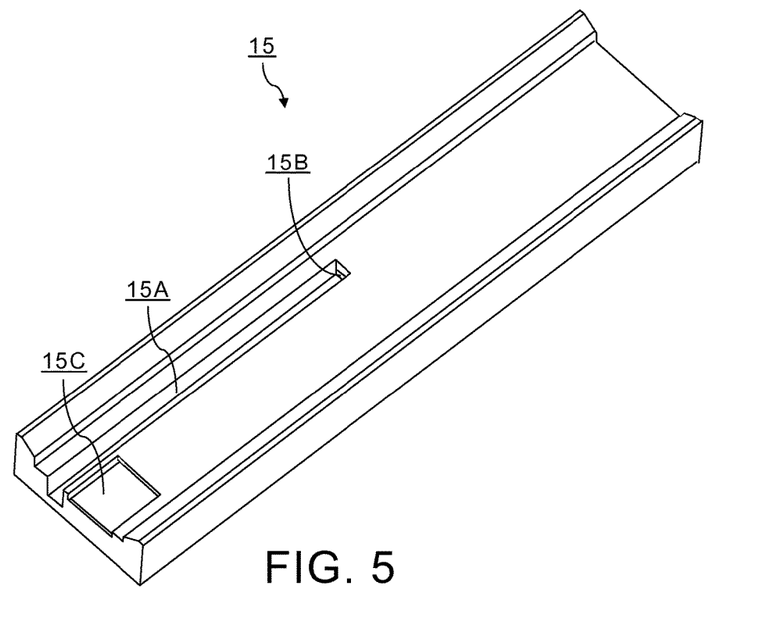
FIG. 5 is a perspective view to show the structure of the bed exterior shown in FIG. 4.

FIG. 4 is a left side view to show a detailed configuration example of the bed apparatus 2 shown in FIG. 1. FIG. 5 is a perspective view to show the structure of the bed exterior 15 shown in FIG. 4.

As shown in FIG. 4 and FIG. 5, the concave portion 15A whose length direction is the movement direction of the table 11 can be formed on the bed exterior 15. The concave portion 15A of the bed exterior 15 may be a rectangular groove fitting with the shape of the cable guide 14. Accordingly, the concave portion 15A having a bottom face is formed on the bed exterior 15.

Furthermore, the length of the concave portion 15A is set to a length which can cover the range in which the downside part of the cable guide 14 may lie. Accordingly, when the end part of the cable guide 14 in the bed supporting part 13 side is fixed to the center of the bed supporting part 13, the concave portion 15A is to be formed from the center of the bed exterior 15 to the end part of the gantry 9 side.

Then, the downside part of the cable guide 14 can be placed in the concave portion 15A of the bed exterior 15. Furthermore, the end part of the cable guide 14 in the bed supporting part 13 side can be fixed to at least one of the bottom face and the lateral faces of the concave portion 15A.

Consequently, the downside part of the cable guide 14 is guided from the three directions of left, right and bottom sides by the concave portion 15A of the bed exterior 15. On the other hand, the upper part of the cable guide 14 is guided from above by the under surface of the table 11. Therefore, it is possible to prevent a gap of the cable guide 14 in the horizontal direction H when the table 11 is moved. Additionally, a space required between the table 11 and the bed exterior 15 can be minimized Furthermore, the first opening part 15B for passing the signal cables 18, going through the cable guide 14, into the bed supporting part 13 is formed in the bed exterior 15. As shown in FIG. 5, it is preferable to form the one first opening part 15B on the wall surface forming the concave portion 15A of the bed exterior 15, from the perspective of preventing a fluid and a foreign substance from entering the bed supporting part 13. Furthermore, from the similar perspective, it is suitable to minimize the size of the first opening part 15B according to the number and the thicknesses of the signal cables 18 and dispose the first opening part 15B near the center of the concave portion 15A. Consequently, since the concave portion 15A of the bed exterior 15 runs to the end part in the gantry 9 side, possibly spilled fluid mostly flows outside the bed apparatus 2.

Further, the second opening part 15C for placing the table driving mechanism 12 in the bed apparatus 2 is formed on the end part of the bed exterior 15 in the gantry 9 side. For example, the second opening part 15C may be disposed in the range of the bed exterior 15 which lies constantly under the table 11. In the example shown by the figures, the second opening part 15C for arranging the table driving mechanism 12 is formed in the bed exterior 15 so as to lie in the end part side of the gantry 9 side from the center position in the longitudinal direction of the bed exterior 15.

Consequently, it becomes possible to maximize the stroke of the table 11 according to the length of the table 11. Furthermore, even in the in-limit condition in which the table 11 has been maximally sent into the gantry 9, the second opening part 15C is covered with the table 11. Therefore, it is possible to prevent a fluid and a foreign substance from entering the bed supporting part 13.

Figure 6:
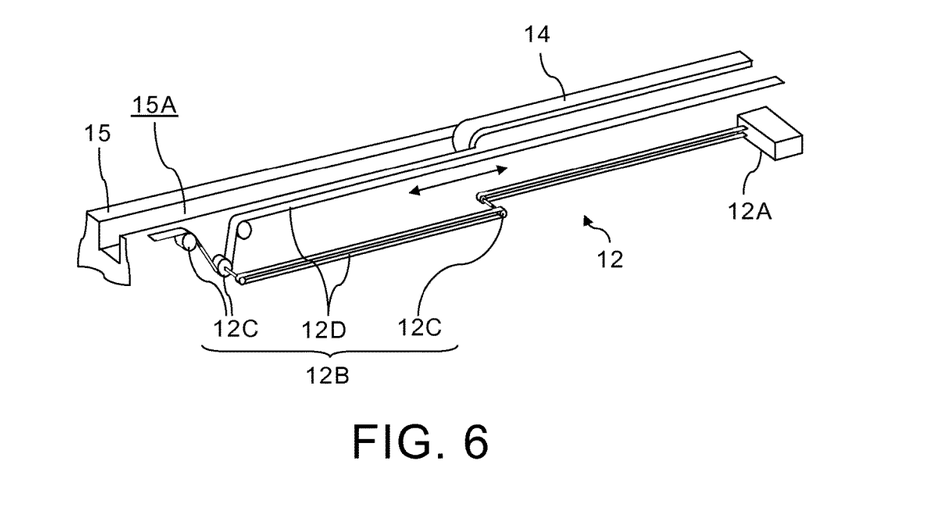
FIG. 6 is a perspective view to show the detailed configuration of the table driving mechanism when the table shown in FIG. 1 is at the out limit position farthest from the gantry.

FIG. 6 is a perspective view to show the detailed configuration of the table driving mechanism 12 when the table 11 shown in FIG. 1 is at the out limit position farthest from the gantry 9. Furthermore, FIG. 7 is a perspective view to show the detailed configuration of the table driving mechanism 12 in the state that the table 11 shown in FIG. 1 has been sent into the gantry 9.

Figure 7:
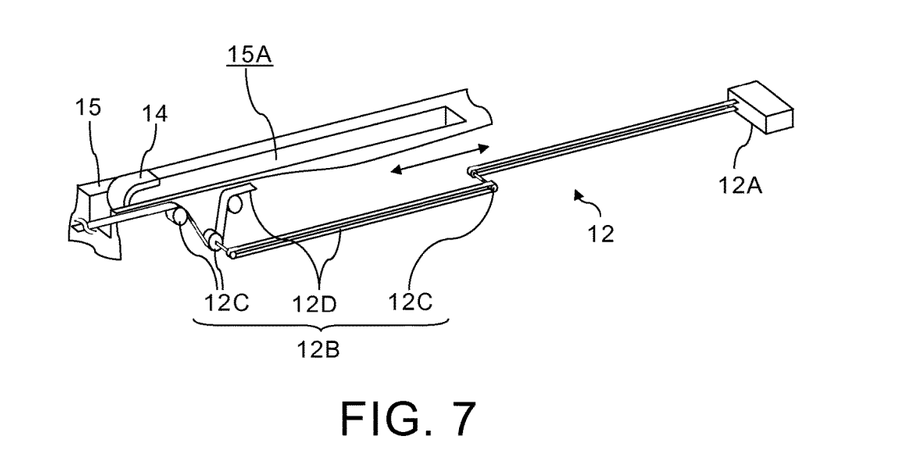
FIG. 7 is a perspective view to show the detailed configuration of the table driving mechanism in the state that the table shown in FIG. 1 has been sent into the gantry.

As shown in the respective figures including FIG. 6 and FIG. 7, the table driving mechanism 12 can be configured using a table driving power source 12A and a power transmission part 12B. A power source such as a motor can be used as the table driving power source 12A. The power transmission part 12B has a function to transmit the power output from the table driving power source 12A to the table 11. Accordingly, the power transmission part 12B is connected with each of the table 11 and the table driving power source 12A.

The power transmission part 12B can be configured with a mechanism, which can change the rotary torque output from the table driving power source 12A into the force for a rectilinear travel, like a power transmission belt moved by rotary shafts or a stick member having a concavo-convex shape coupling with a gear wheel. Note that, in the respective figures, the power transmission part 12B configured with plural power transmission belts 12D connected mutually via the rotary shafts 12C is exemplified. Each of the power transmission belts 12D can be attached to the table 11 in the longitudinal direction by plural attaching implements 12E each having a rectangular-tray-shaped section.

Each of the power transmission belts 12D of the power transmission part 12B is configured to move in the length direction of the concave portion 15A without touching any of the cable guide 14 and the wall surfaces forming the concave portion 15A of the bed exterior 15. The respective figures show an example that the power transmission belts 12D are arranged to become parallel to the concave portion 15A of the bed exterior 15. Consequently, it is possible to avoid the interference of the power transmission belts 12D with each of the cable guide 14 and the concave portion 15A of the bed exterior 15 and to transmit the power generated in the table driving power source 12A to the table 11 without troubles.

Specifically, a motor as the table driving power source 12A rotates and the power transmission belt 12D connected to the output shaft of the motor is moved in the length direction. Then, the power is transmitted to the respective power transmission belts 12D sequentially via the respective rotary shafts 12C. Consequently, the table 11 moves by movement of the power transmission belts 12D attached to the table 11 in the length direction.

Note that, when the power transmission part 12B is configured with another mechanism, the power transmission part 12B is configured to move in the length direction of the concave portion 15A similarly without touching any of the cable guide 14 and the wall surfaces forming the concave portion 15A of the bed exterior 15.

Furthermore, the rotary shafts 12C for moving the table 11 can be placed at the end part of the bed supporting part 13 in the gantry 9 side. Meanwhile, the table driving power source 12A can be placed at the end part of the bed supporting part 13 in the opposite side to the side to which the table 11 is sent, i.e., the opposite side to the gantry 9. Consequently, it is possible to reduce an adverse effect on the table driving power source 12A by a magnetic field generated by the static magnetic field magnet 4. Specifically, a failure and malfunctions of the table driving power source 12A can be prevented while securing the stroke of the table 11 by keeping only the table driving power source 12A away from the static magnetic field magnet 4.

In addition, a guard member for safety to narrow the gap between the table 11 and the bed supporting part 13 can be mounted to the end part of the table 11 in the opposite side to the gantry 6 though an illustration is being omitted in FIG. 4 and the like.

Figure 8:
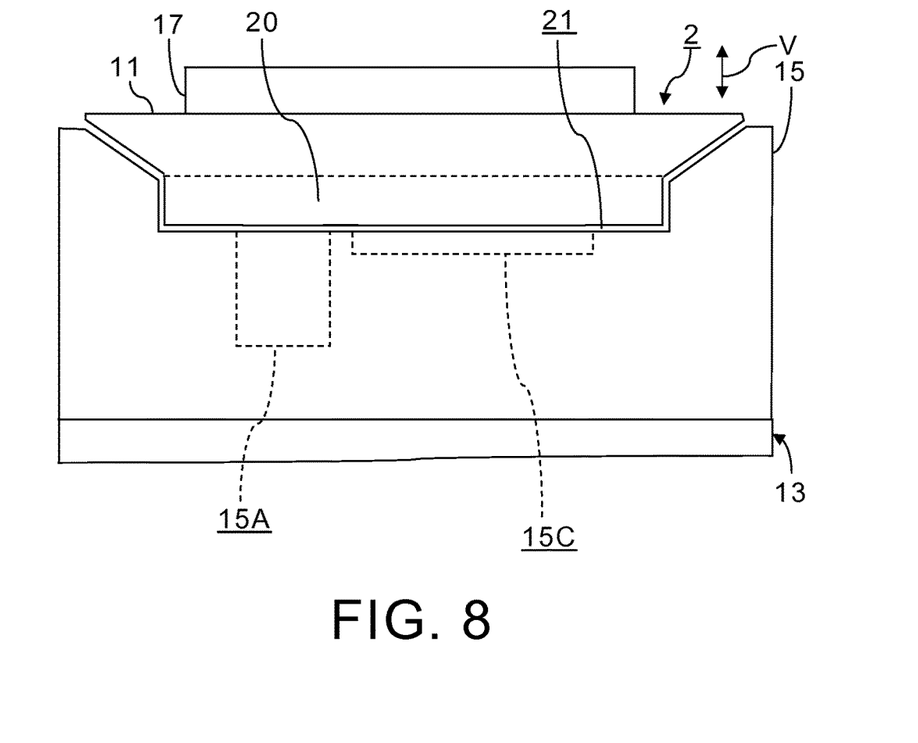
FIG. 8 shows an example of mounting a guide member to the table 11 shown in FIG. 1.

FIG. 8 shows an example of mounting a guide member to the table 11 shown in FIG. 1.

FIG. 8 is a view of a state, where the table 11 has been set on the bed supporting part 13, as viewed from the side opposite to the gantry 9. As shown in FIG. 8, the guard member 20 can be mounted to the end part of the table 11. Then, a gap 21 between the bed supporting part 13 and the table 11 in the state that the table 11 has been set on the bed supporting part 13 can be narrowed and equalized by the guard member 20. In the example shown in the figure, the plate guard member 20 along the shape of the bed exterior 15 is set to the end part of the table 11 as a guard wall.

Consequently, it is possible to prevent a foreign substance from entering the gap between the bed supporting part 13 and the table 11. The guard member 20 as described above can be connected to the body of the table 11, on which the connection port 17 for a reception coil is provided, as a component of the table 11 with a connection member. Alternatively, the guard member 20 may be formed as a part of the table 11 by integral molding.

That is, in the bed apparatus 2 as described above, the cable guide 14 for protecting the signal cables 18 between the table 11 and the bed supporting part 13 is configured and arranged to bend in the vertical direction V. Further, the bed apparatus 2 is configured to have the concave portion 15A, for guiding the cable guide 14, on the bed exterior 15.

Therefore, according to the bed apparatus 2, the structures of the cable guide 14, the bed exterior 15 and the table driving mechanism 12 can be simplified. Consequently, the manufacturing cost of the bed apparatus 2 can be reduced. Especially, the bed exterior 15 can be configured integrally with a single member. Accordingly, provided the bed exterior 15 is made to have the monocoque structure, the bed exterior 15 can be easily manufactured by a forming process. In this case, an amount of strain can be reduced compared to a bed exterior manufactured by forming resin. Furthermore, since the structures of not only the bed exterior 15 but also the cable guide 14 and the table driving mechanism 12 become simple, the quality thereof can be improved.

Further, influence on the table driving mechanism 12 by setting the cable guide 14 is small. Accordingly, the table driving power source 12A can be placed at the opposite side to the gantry 9 of the bed apparatus 2. Consequently, failures and malfunctions of the table driving power source 12A can be prevented.

Furthermore, the number and sizes of opening parts formed in the bed exterior 15 can be reduced. Accordingly, it is possible to prevent a fluid and a foreign substance from entering the bed apparatus 2.

In addition, it becomes easy to lift up the table 11 and it becomes possible to reduce a work required for maintenance of the bed apparatus 2.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A bed apparatus for a magnetic resonance imaging apparatus, said bed apparatus comprising:
   a table providing a connection port for a reception coil of magnetic resonance signals;
   a table driving mechanism configured to shift said table longitudinally along a horizontal direction;
   a bed supporting part configured to support said table there-above; and
   a cable guide configured to protect a signal cable disposed under said table and connected at one end to said connection port as the cable passes between said table and said bed supporting part by bending successive portions of the signal cable in a vertical direction transverse to longitudinal movement of said table as the table is moved to respectively corresponding different positions in the horizontal direction;
   wherein
   said cable guide is configured to permit vertical lifting of the table from the bed supporting part while the cable is still connected to said connection port;
   one end of said cable guide is connected to an underside of said table adjacent said connection port;
   said bed supporting part includes an upwardly-facing rectilinear concavity extending horizontally parallel to longitudinal movements of the table located there-above, said concavity having side-walls and a bottom which provide guidance to moving lower portions of said cable guide housed in said concavity as the table is moved in the horizontal direction;
   a second end of said cable guide is connected to the bed supporting part adjacent an opening; and
   said signal cable passes through said opening in an end face of the concavity located between ends of the bed supporting part.

2. The bed apparatus for a magnetic resonance imaging apparatus as in claim 1, wherein said table driving mechanism has:
   a table driving power source; and
   a power transmission part configured to transmit a power output from said table driving power source to said table by moving in the length direction of the concave portion without contacting said cable guide and a wall surface forming the concave portion, said power transmission part being connected to said table.

3. The bed apparatus for a magnetic resonance imaging apparatus as in claim 2,
   wherein said table driving power source is located at an end part of said bed supporting part, the end part being at an opposite side from a side to which said table is sent outwardly.

4. The bed apparatus for a magnetic resonance imaging apparatus as in claim 1, wherein said cable guide has:
   tubal members each having two open ends; and
   connection members each configured to connect adjacent tubal members while leaving a gap between adjacent tubal members to permit one of the adjacent tubal members to be inclined with respect to another.

5. The bed apparatus for a resonance imaging apparatus as in claim 1, wherein said table has a guard member at an end of said table, the guard member being configured to define a uniform gap between said bed supporting part and said table in a state where said table has been set on said bed supporting part.

6. A bed apparatus for a magnetic resonance imaging apparatus, said bed apparatus comprising:
   a table providing a connection port for a reception coil of magnetic resonance signals;
   a table driving mechanism configured to shift said table in a longitudinal horizontal direction;
   a bed supporting part configured to support said table there-above; and
   a cable guide configured to protect a signal cable disposed under said table and connected at one end to said connection port as the cable passes between said table and said bed supporting part by bending successive portions of the signal cable along with longitudinal movement of said table as the table is moved to respectively corresponding different positions in the horizontal direction;
   wherein
   said bed supporting part has an opening for accommodating said table driving mechanism, the opening being located under said table irrespective of the longitudinal position of said table,
   said cable guide is configured and disposed to permit vertical lifting of the table from the bed supporting part while the cable is still connected to said connection port;
   one end of said cable guide is connected to an underside of said table adjacent said connection port;
   said bed supporting part includes an upwardly-facing rectilinear concavity extending horizontally parallel to longitudinal movements of the table located there-above, said concavity having side-walls and a bottom which provide guidance to moving lower portions of said cable guide housed in said concavity as the table is moved in the horizontal direction; and
   a second end of said cable guide is connected to the bed supporting part adjacent a second opening, through which said signal cable passes, in an end face of the concavity located between ends of the bed supporting part.

7. A magnetic resonance imaging (MRI) apparatus comprising:
   a bed apparatus as in claim 1; and
   an (MRI) gantry configured to image an object set on said bed apparatus.

8. The bed apparatus for a magnetic resonance imaging apparatus as in claim 1 wherein:
   said bed supporting part includes an upwardly-facing concavity located at an end of the bed supporting part nearest a magnetic resonance imaging apparatus gantry when in use that is covered by the table even when the table is maximally moved longitudinally into the gantry; and said table driving mechanism is accommodated within said concavity.

9. The bed apparatus for a magnetic resonance imaging apparatus as in claim 6 wherein:

said opening in the bed supporting part for accommodating said table driving mechanism comprises an upwardly-facing concavity located at an end of the bed supporting part nearest a magnetic resonance imaging apparatus gantry when in use that is covered by the table even when the table is maximally moved longitudinally into the gantry; and said table driving mechanism is accommodated within said upwardly-facing concavity for accommodating said table driving mechanism.

* * * * *